United States Patent
Kajiya et al.

(10) Patent No.: US 8,367,124 B2
(45) Date of Patent: Feb. 5, 2013

(54) LYMPHATIC VESSEL STABILIZER

(75) Inventors: Kentaro Kajiya, Yokohama (JP);
Masahiro Ota, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 66 days.

(21) Appl. No.: 12/737,203

(22) PCT Filed: Jun. 17, 2009

(86) PCT No.: PCT/JP2009/061047
§ 371 (c)(1),
(2), (4) Date: Dec. 17, 2010

(87) PCT Pub. No.: WO2009/154237
PCT Pub. Date: Dec. 23, 2009

(65) Prior Publication Data
US 2011/0091584 A1 Apr. 21, 2011

(30) Foreign Application Priority Data
Jun. 18, 2008 (JP) .................................. 2008-159623

(51) Int. Cl.
*A01N 65/00* (2009.01)
(52) U.S. Cl. ...................................................... 424/725
(58) Field of Classification Search .................... None
See application file for complete search history.

(56) References Cited

U.S. PATENT DOCUMENTS
6,607,756 B1  8/2003 Rosenstiel
2007/0117864 A1 5/2007 Yagasaki et al.

FOREIGN PATENT DOCUMENTS
CN      1104113      *  6/1995
CN      1893939 A       1/2007
WO   WO 2008/059310 A1  5/2008

OTHER PUBLICATIONS

Botantical.com, 4 pages, 2012.*
Mohammad Akbar Arzani, Qaraabaadeen Qaadri (17th Century AD), Ahmadi Publication, Delhi, 1968, p. 288 (Exhibit 1 of Third Party Observations filed against corresponding EP 0976685.3/EP 2319537 on Aug. 11, 2011).
Mohammad Shareef Kahn, Ilaaj-al-Amraaz (18th Century AD), Afzal-al-Matabe, Barqi Press, Delhi, 1921, p. 324 (Exhibit 2 of Third Party Observations filed against corresponding EP 09766685.3/EP 2319537 on Aug. 11, 2011).
Mohammad Akmal Khan Qaraabaadeen Azam wa Akmal (20th Century AD), Matba Siddiqi, Delhi/Matba Mustafai, Delhi, 1909, p. 8 (Exhibit 3 of Third Party Observations filed against corresponding EP 09766685.3/EP 2319537 on Aug. 11, 2011).
Mohammad Akbar Arzani, Qaraabaadeen Qaadri (17th Centruy AD), Ahmadi Publication, Delhi, 1968, p. 368 (Exhibit 4 of Third Party Observations filed against corresponding EP 09766685.3/EP 2319537 on Aug. 11, 2011).
Yugi; Yigi Munivar Vaithiya Chinthamani, Pub: Palani Thandayuthapani Devasthanam publications, Directorate of Indian Systems of Medicine, Chennai, (Edn: 2nd) 1976, p. 221 (Exhibit 5 of Third Party Observations filed against corresponding EP 09766685.3/EP 2319537 on Aug. 11, 2011).
Agasthiyar: Agathiyar vaithia kaviyam, 1500,Pub: Rathina Nayakar & Sons, Thirumagal Vilakku Press, Chennai, 1952, p. 177-179 (Exhibit 6 of Thid Party Observations filed against corresponding EP 09766685.3/EP 2319537 on Aug. 11, 2011).
Yugi; Yugi Munivar Vaithiya Chinthamani, Pub: Palani Thandayuthapani Devasthanam Publications, Directorate of Indian Systems of Medicine, Chennai, (Edn. 2nd) 1976, p. 357.
Nishibe et al., "Phenolic Compounds from Stem Bark of *Acanthopanax senticosus* and Their Pharmacological Effect in Chronic Swimming Stressed Rats," Chem. Pharm. Bull, 1990, 38(6):1763-1765.
Shimada et al., "Extract Prepared from the Bark of *Cinnamomum cassia* Blume Prevents Glutamate-induced Neuronal Death in Cultured Cerebellar Granule Cells," Phytotherapy Research. 2000, 14:466-468.
Gale et al., "Antiopoietin-2 is Required for Postnatal Angiogenesis and Lymphatic Patterning, and Only the Latter Role is Rescued by Angiopoietin-1," Developmental Cell, Sep. 2002, 411-423.
Tammela et al., Antiopoietin-1 promotes lymphatic sprouting and hyperplasia, Blood, Jun. 15, 2005, 105(12):4642-4648.
Database WPI Week 200882, Thomson Scientific, London, GB, AN 2008-013532; English abstract of KR 2008 0025710 A, Mar. 21, 2008.
Jung et al., "In Vivo Anti-Inflammatory and Antinociceptive Effects of Liriodendrin Isolated from the Stem Bark of *Acanthopanax senticosus*," Planta Medica, Jul. 1, 2003, 69(7):610-616.
Database TKDL [Online], dated 1811, "Habb Waasli," XP00266404, Accession No. MH5/2791, one page, with English translation, 2 pages.
Database TKDL [Online], dated 1811, "Itreefal Ghudadi," XP00266405, Accession No. MH1/3719, one page, with English translation, 2 pages.
Database TKDL [Online], dated 1911, "Kukkilathy Vadakam," XP00266406, Accession No. GP03/245, one page, with English translation, 2 pages.

*Primary Examiner* — Michael Meller
(74) *Attorney, Agent, or Firm* — Foley & Lardner LLP

(57) ABSTRACT

Provided is a lymphatic vessel stabilizer composed of Tie2 activator. The Tie2 activator is preferably at least one type selected from the group consisting of angiopoietin 1 (Ang-1), extract of *Cinnamomum* species plants, extract of Siberian Ginseng and syringaresinol.

5 Claims, 2 Drawing Sheets

LYMPHATIC VESSEL STABILIZER

CROSS-REFERENCE TO RELATED APPLICATIONS

This application is a National Stage application of PCT/JP2009/061047, filed Jun. 17, 2009, which claims priority from Japanese application JP 2008-159623, filed Jun. 18, 2008.

TECHNICAL FIELD

The present invention provides a lymphatic vessel stabilizer composed of a Tie2 activator (phosphorylation agent).

BACKGROUND ART

Blood is sent out from the heart and passes through capillaries and veins after which it returns to the heart. Lymphatic vessels are vessels that form pathways for discharging tissue fluid separate from this circulation system. Lymphatic vessels maintain blood volume at a constant level and maintain a closed circulatory system by returning interstitial fluid, protein, fat, cells and the like that have leaked from blood vessels in peripheral tissues to the vascular system. In capillaries present in skin, the outsides of endothelial cells are surrounded by a basement membrane, and pericytes are further attached thereto. On the other hand, in lymphatic capillaries, there is hardly any basement membrane surrounding the outsides of endothelial cells and pericytes are not attached thereto. This structure is useful for efficiently incorporating body fluid and cells from the interstitium (Non-Patent Document 1). The tyrosinase-related receptor, vascular endothelial growth factor receptor 3 (VEGFR-3), has previously been shown to be specifically expressed in lymphatic endothelial cells, and its ligands in the form of VEGF-C and VEGF-D have been shown to induce lymphangiogenesis. In addition, VEGF-A has been clearly demonstrated to induce lymphangiogenesis mediated by VEGFR2 expressed in lymphatic endothelial cells (Non-Patent Document 2). Moreover, an example of a report describing lymph duct function is indicated below. Although prominent lymphangiogenesis was observed in mouse ear infected with adenovirus expressing VEGF-A, in addition to structural abnormalities, lymphatic vessel recovery function was clearly determined to be inhibited considerably based on the results of an experiment in which colloidal carbon was injected into the ear (Non-Patent Document 3). In other words, it is thought that lymphatic vessels are required to be suitably arranged and lined with lymphatic endothelial cells in order to function. We have defined this as "lymphatic vessel stabilization".

Physical or chemical stimulation of skin induces vascular permeability due to angiogenesis, VEGF-A and the like, resulting in accumulation of tissue fluid and the occurrence of edema. On the other hand, these stimuli are also known to directly induce neogenesis and dilation of lymphatic vessels. Lymphatic vessel dilation has been observed to be induced by ultraviolet inflammation, while experiments involving injection of dye have clearly demonstrated that lymphatic vessel function is inhibited. Lymphatic vessels are thought to dilate in an attempt to recover interstitial fluid accompanying leakage of moisture into the dermis accompanying vasodilation. However, excessive lymphatic vessel dilation is also thought to delay edema by conversely lowering its recovery function (Non-Patent Document 4). In other words, "lymphatic vessel stabilization", that does not induce excessive lymphatic vessel dilation is thought to be required for rapid recovery of interstitial fluid.

Examples of pathological states that have previously been known to involve lymphatic vessel dysfunction include congenital lymphedema as well as secondary lymphedema associated with filariasis, surgery, malignant tumors and inflammation. Examples of congenital lymphedema include Milroy's disease, Meige's disease and lymphedema-distichiasis syndrome. Lymphatic vessel aplasia or hypoplasia has been reported in Milroy's disease, while lymphatic vessel hyperplasia has been reported in lymphedema-distichiasis syndrome. On the basis of these findings as well, it is thought to be necessary to retain recovery function through not only lymphangiogenesis, but also lymphatic vessel stabilization (Non-Patent Document 5).

PRIOR ART DOCUMENTS

Non-Patent Documents

Non-Patent Document 1: Jikken Igaku (Experimental Medicine), Vol. 24, No. 18 (2006), pp. 133-138
Non-Patent Document 2: Jussila, L. and Alitalo, K.: (2006) Vascular growth factors and lymphangiogenesis, Physiol. Rev., 82, 673-700
Non-Patent Document 3: Nagy, et al.: (2002) Vascular permeability factor/vascular endothelial growth factor induces lymphangiogenesis as well as angiogenesis, J. Exp. Med., 196, 1497-1506
Non-Patent Document 4: Kajiya, K., Hirakawa, S. and Detmar, M.: (2006) VEGF-A mediates UVB-induced impairment of lymphatic vessel function, Am. J. Pathol., 169, 1496-1503
Non-Patent Document 5: Experimental Medicine, Vol. 24, No. 18 (2006), pp, 139-143
Non-Patent Document 6: Kajiya, K., et al.: (2005) Hepatocyte growth factor promotes lymphatic vessel formation and function, EMBO. J., 24, 2885-95
Non-Patent Document 7: Experimental Medicine, Vol. 20, No. 8 (2002), pp. 52-57

SUMMARY OF THE INVENTION

Technical Problem

An object of the present invention is to provide a drug effective for maintaining and accelerating lymphatic vessel recovery function through lymphatic vessel stabilization.

Means for Solving the Problems

Following the molecular cloning of VEGF, molecules of the VEGF family and angiopoietin (Ang) family have been successively identified as factors that specifically act on blood vessel formation. VEGF and its receptors are involved in an extremely wide range of blood vessel formation extending from the initial formation of blood vessels referred to as vasculogenesis to it subsequent angiogenesis. On the other hand, Ang functions in lumen formation accompanying cellular phenomena such as budding, branching, invagination and regression by vascular endothelial cells following vasculogenesis. Ang controls adhesion between vascular endothelial cells and vascular wall cells such as pericytes and vascular smooth muscle cells mediated by receptor-related tyrosine kinase with Ig and EGF homology domain 2 (Tie2) expressed in vascular endothelial cells, and although it is understood to function in stabilizing vascular structure (Non-Patent Document 7), the relationship between Tie2 and lymphatic vessels has not been adequately elucidated.

When the inventors of the present invention conducted an investigation focusing on the relationship between Ang-1 and Tie2 expressed in lymphatic endothelial cells, it was found that Ang-1 promotes the recovery function of lymphatic vessels mediated by activation of Tie2, thereby leading to completion of the present invention as described below:
(1) a lymphatic vessel stabilizer consisting of a Tie2 activator;
(2) the lymphatic vessel stabilizer of (1), wherein the Tie2 activator is at least one type selected from the group consisting of angiopoietin 1 (Anq-1), extract of *Cinnamomum* species plants, extract of Siberian Ginseng and syringaresinol;
(3) the lymphatic vessel stabilizer of (2), wherein the extract is derived from *Cinnamomum cassia* Blume;
(4) the lymphatic vessel stabilizer of (2), wherein the extract is derived from cinnamon twig or cinnamon bark;
(5) the lymphatic vessel stabilizer of any of (2) to (4), wherein the extract is an aqueous extract; and,
(6) a cosmetic method for improving or preventing swelling, comprising application of the lymphatic vessel stabilizer of any of (1) to (5).

Effects of the Invention

Use of the lymphatic vessel stabilizer relating to the present invention makes it possible to improve and/or prevent swelling and the like.

EMBODIMENTS OF THE INVENTION

Figure 1:
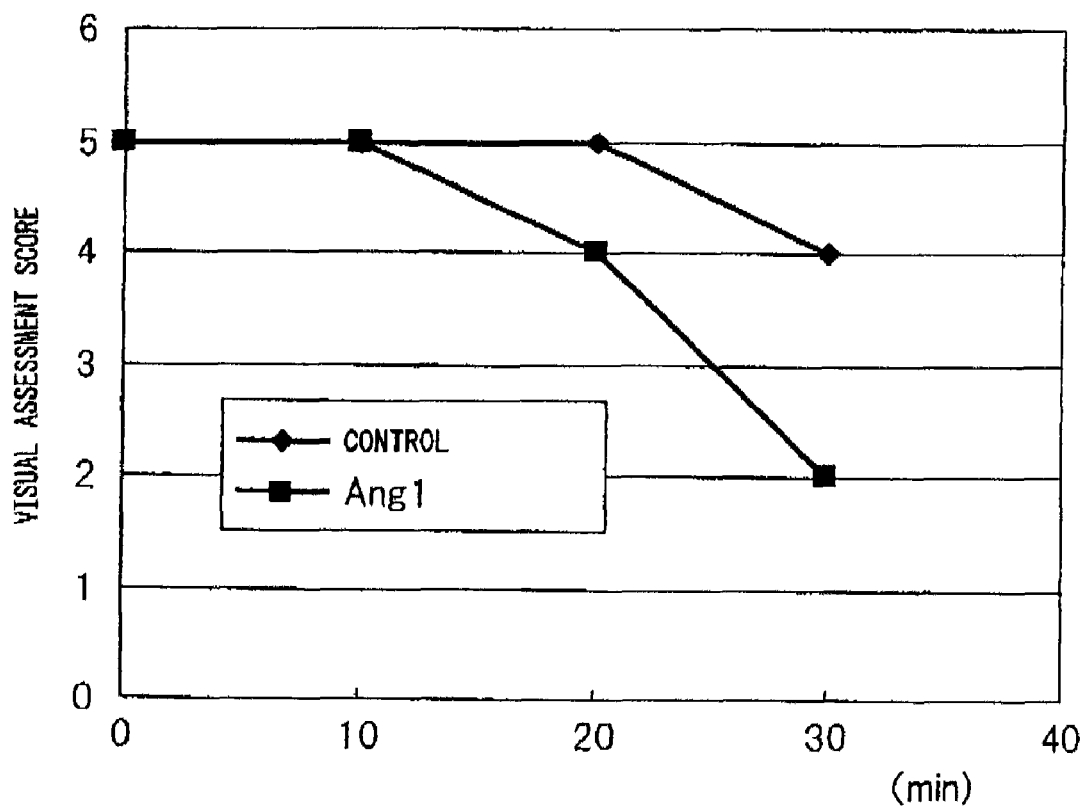
FIG. 1 is a graph in which changes in recovery function in lymphatic vessels induced by Ang-1 were scored based on a visual assessment.

Although there are no particular limitations on the Tie2 activator, examples include commonly known Tie2 activators such as angiopoietin 1 that have activity that activates Tie2, and Tie2 activators that were newly found to have that activity by the inventors of the present invention, such as extracts of *Cinnamomum* species plants, Siberian Ginseng extract or syringaresinol. Furthermore, activation of Tie2 as described here refers to the ability to be able to convert Tie2 to its active form (phosphorylated Tie2) by phosphorylation.

Members of the genus *Cinnamomum* refer to plants belonging to the order Lauraceae, family Lauraceae, and consist of more than 300 species, known examples of which include *Cinnamomum cassia* Blume, *C. camphora, C. daphnoides, C. doederleinii, C. japonicum, C. pseudopedunculatum, C. sieboldii, C. verum* and *C. zeylanicum*. Preferably an extract derived from *Cinnamomum cassia* Blume, and particularly preferably an extract derived from cinnamon twig, which is a young branch of *Cinnamomum cassia* Blume, or cinnamon bark, is used for the Tie2 activator in the present invention. Although extracts of cinnamon bark are known to be useful as an active ingredient of hair tonics (Japanese Unexamined Patent Publication No. H10-265350), its lymphatic vessel stabilization activity has been heretofore completely unknown.

Siberian Ginseng extract has traditionally been said to be effective for physical or mental restoration. This extract is extremely effective for decreased mental and physical abilities such as weakness, extreme fatigue or decreased concentration as well as recovery following illness. It is used in the U.S. as a diet supplement.

The aforementioned extract can be obtained according to ordinary methods, and for example, can be obtained by immersing or heat-refluxing a source plant with an extraction solvent either at normal temperatures or while heating followed by filtration and concentration. Any solvent can be used for the extraction solvent provided it is a solvent that is ordinarily used for extraction, examples include aqueous solvents such as water, physiological saline, phosphate buffer or borate buffer, and organic solvents including alcohols such as ethanol, propylene glycol, 1,3-butylene glycol or glycerin, water-containing alcohols, chloroform, dichloroethane, carbon tetrachloride, acetone, ethyl acetate and hexane, and these can be used alone or in combination. Water is preferably used for the solvent. Extracts obtained by extracting with the aforementioned solvents can be used as is, can be used in the form of a concentrated extract obtained by concentrating by freeze-drying and the like, can be used after removing impurities by using adsorption or an ion exchange resin and the like, or can be adsorbed with a porous polymer column (such as Amberlite XAD-2) followed by eluting with a desired solvent and then further concentrating.

Syringaresinol is an antioxidant lignan compound unique to plants, and is used in foods, beverages and pharmaceuticals due to its hypertension ameliorative effect and its inhibitory effect on Helicobacter pylori (see, for example, Japanese Unexamined Patent Publication No. H8-268887 and Japanese Unexamined Patent Publication No. 2004-352652). Syringaresinol has the chemical structure indicated below.

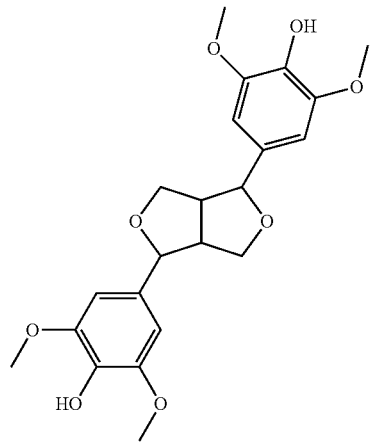

Syringaresinol is a known compound, and is contained in *Cinnamomum cassia* Blume of the order Laurales, family Lauraceae, and particularly in young branches (cinnamon twig) or bark (cinnamon bark) thereof. However, its effects of stabilizing lymphatic vessels and activating Tie2 are completely unknown. Syringaresinol may be extracted from a natural source such as cinnamon twig or cinnamon bark, or may be synthesized.

Syringaresinol may be in the form of an inorganic salt or organic salt. Examples of salts include, but are not limited to, inorganic salts such as hydrochlorides, sulfates, phosphates, hydrobromides, sodium salts, potassium salts, magnesium salts, calcium salts or ammonium salts. Examples of organic salts include acetates, lactates, maleates, fumarates, tartrates, citrates, methanesulfonates, p-toluenesulfonates, triethanolamine salts, diethanolamine salts and amino acid salts.

The lymphatic vessel stabilizer relating to the present invention can be used as a pharmaceutical or cosmetic effective for treating and/or preventing various, skin diseases such as edema (swelling) attributable to leakage of lymph caused by structural instability of lymphatic vessels. Examples of edema include secondary lymphedema associated with ultraviolet radiation, filariasis, surgery, malignant tumors and inflammation, and congenital lymphedema such as Milroy's disease, Meige's disease and lymphedema-distichiasis syndrome.

The lymphatic vessel stabilizer relating to the present invention is also used in a cosmetic method for diminishing and/or preventing swelling or bags under the eyes. This cosmetic method can be carried out by, for example, applying the lymphatic vessel stabilizer relating to the present invention to a site where there is swelling and the like, and either allowing to stand as is or promoting the flow of lymph by massaging in the direction of lymph flow. Examples of locations where this method is applied include sites covering the entire body such as the face, neck, hands and feet.

The dose, application method and form of the lymphatic vessel stabilizer relating to the present invention can be suitably determined according to the purpose of use thereof. For example, there are no particular limitations on the administration form of the lymphatic vessel stabilizer of the present invention, and although it may be in the form of oral administration, parenteral administration or external application, it is preferably in the form of external application. Examples of drug forms include external preparations such as ointment, cream, milky lotion, lotion, facial pack or bath additive, parenteral preparations such as an injection preparation, infusion preparation or suppositories, and oral preparations such as tablets, powders, capsules, granules, extract or syrup. Moreover, another example of an application of the lymphatic vessel stabilizer relating to the present invention is a functional food.

Although the incorporated amount of Tie2 activator in the lymphatic vessel stabilizer of the present invention can be suitably determined corresponding to the application, it is typically 0.0001 to 20 mol % and preferably 0.0001 to 10.0 mol % based on the total amount of the preparation.

In addition, a vehicle, desiccant, preservative, reinforcing agent, thickener, emulsifier, antioxidant, sweetener, sour flavoring, seasoning, colorant or fragrance ordinarily used in foods and pharmaceuticals, or a whitening agent, moisturizer, oily component, ultraviolet absorber, surfactant, thickener, alcohol, powdered component, colorant, aqueous component, water or various types of skin nutrients typically used in cosmetics can be suitably incorporated as necessary in the lymphatic vessel stabilizer of the present invention in addition to the Tie2 activator.

Moreover, in the case of using the lymphatic vessel stabilizer of the present invention as an external skin preparation, a commonly used assistant can be suitably incorporated in the external skin preparation, examples of which include metal chelating agents such as disodium edetate, trisodium edetate, sodium citrate, sodium polyphosphate, sodium metaphosphate or gluconic acid, drugs such as caffeine, tannin, verapamil, tranexamic acid and derivatives thereof, licorice extract, glabridin, hot water extract of quince fruit, various herbal medicines, tocopherol acetate or glycyrrhizic acid and derivatives or salts thereof, whitening agents such as vitamin C, magnesium ascorbyl phosphate, ascorbic acid glucoside, albutin or kojic acid, sugars such as glucose, fructose, mannose, sucrose or trehalose, and vitamin A substances such as retinoic acid, retinol, retinol acetate or retinol palmitate.

EXAMPLES

The following provides a more detailed explanation of the present invention through examples thereof. Furthermore, the present invention is not limited by these examples. Incorporated amounts are indicated as percent by weight (wt %).

Experimental Methods

Lymph Drainage Assay

The auricles of 8-week-old mice were infected with adenovirus ($1 \times 10^9$ ifu/mouse), in which mouse-derived angiopoietin-1 (Ang-1) gene was incorporated into an AdenoX vector, with a Hamilton syringe (Hamilton, Reno. NV). Mice were also infected with adenovirus incorporating only AdenoX vector as a control. 1 µl of colloidal carbon solution (Kamei Co., Ltd., Japan) was injected into the tip of the auricle with a Hamilton syringe followed by analysis of time-based changes in the flow of lymph. As a result, lymphatic vessel recovery function was observed to be promoted in the ears of mice highly expressing Ang1 (data not shown). In addition, a visual assessment of changes in lymphatic vessel recovery function was also carried out, and comparisons were made by scoring to one of levels (5: all ink remaining in lymphatic vessels, 1: all ink recovered and no longer present in lymphatic vessels), the results of which are shown in FIG. 1. On the basis of FIG. 1, remarkable promotion of lymphatic vessel recovery function was observed in comparison with the control due to expression of the Tie2 activator, Ang-1, thus demonstrating that lymphatic vessels are stabilized by activation of Tie2.

In addition, after sacrificing the animals by anesthesia, the ears of the animals were simultaneously collected and crushed in liquid nitrogen followed by extraction of protein with Phosphosafe Extraction Reagent (Novagen, Madison, Wis.). The total amount of protein was determined with the RC DC Protein Assay Kit (BIO-RAD, Hercules, Calif.) and detected by Western blotting in the manner described below. An equal amount of total protein was subjected to SDS-PAGE with 15% acrylamide gel (NPU-7.5L, ATTO, Japan), and protein expression of Ang-1 was confirmed by staining with an ECL Kit using Ang-1 antibody (Santa Cruz Biotechnology, Santa Cruz, Calif.).

Western Blotting of Lymphatic Endothelial Cells

Lymphatic endothelial cells were isolated from human infant foreskin as CD31-positive, CD34-negative, CD45-negative cells (Non-Patent Document 6). The lymphatic endothelial cells were cultured in EBM-2 (Cambrex, Verviers, Belgium) supplemented with addition factors, and protein was extracted with Phosphosafe Extraction Reagent (Novagen, Madison, Wis.) in the presence of various drugs (Ang-1, cinnamon bark extract, Siberian Ginseng extract and syringaresinol). Cells supplemented with DMSO were prepared as a control.

Figure 2:
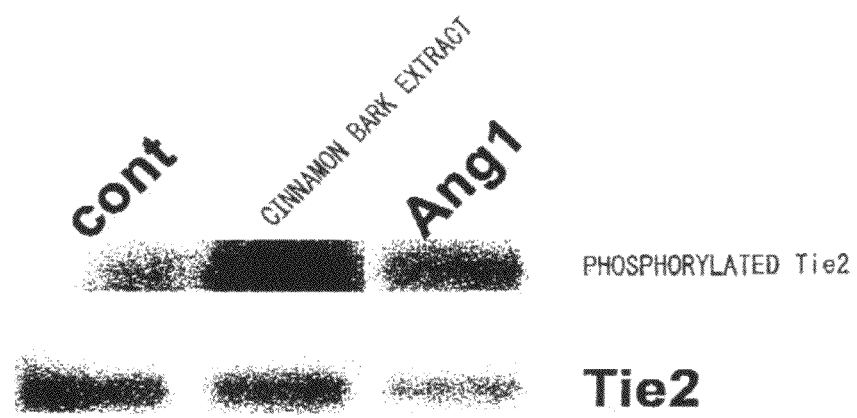
FIG. 2 shows the results of Tie2 phosphorylation by cinnamon bark extract.
Figure 3:
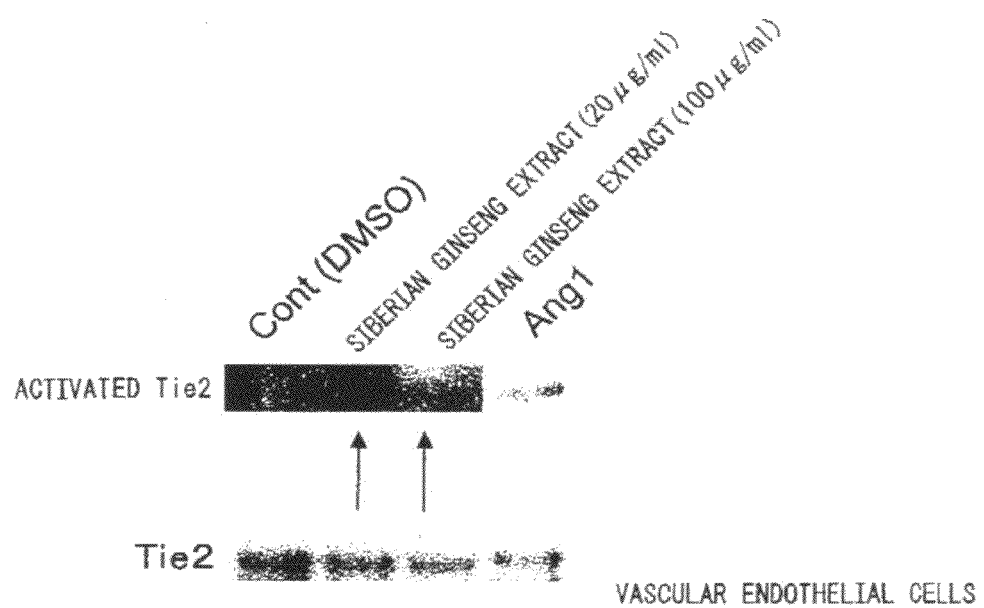
FIG. 3 shows the results of Tie2 phosphorylation by Siberian Ginseng.

Furthermore, the cinnamon bark extract and syringaresinol were prepared in the manner indicated below. The Siberian Ginseng extract (Ask Intercity) was obtained by extracting Siberian Ginseng root with 30% ethanol. This extract was confirmed to contain 1.01% by weight syringaresinol by HPLC. This extract was then dissolved with DMSO for use as each test sample. The total amount of protein was determined with the RC DC Protein Assay Kit (BIO-RAD, Hercules, Calif.), and detected by Western blotting in the manner described below. An equal amount of total protein was subjected to SDS-PAGE using 7.5% acrylamide gel (NPU-7.5L, ATTO, Japan), and expression of Tie2 and phosphorylated Tie2 protein was confirmed by staining with an ECL Kit using Ang-1 antibody (Santa Cruz Biotechnology, Santa Cruz, Calif.). FIG. 2 shows that cinnamon bark extract phosphorylates (activates) Tie2 in the same manner as Ang-1. FIG. 3 shows that Siberian Ginseng extract phosphorylates (activates) Tie2 in the same manner as Ang-1. Furthermore, although the data is not shown, syringaresinol was also confirmed to activate Tie2 in the same manner as Ang-1.

Preparation of Cinnamon Twig Hot-Water Extract Dry Residue 400.7 g of cinnamon twig (*Cinnamomum cassia* Blume) were added to 2 L of water followed by heating and extracting for 3 hours and filtering. 2 L of water were added to the resulting residue followed by repeating the same procedure and heating and extracting two more times. The resulting liquid was freeze-dried to obtain 37.9 g of a hot water extract dry residue.

Fractionation and Isolation of Hot Water Extract Dry Residue 31.0 g of the hot water extract dry residue were subjected to crude fractionation using Sephadex LH-20 (Amersham Pharmacia Biotech AB). An aqueous solution fraction (2.7 g), 50% methanol eluted fraction (8.5 g), methanol eluted fraction (4.9 g), acetone eluted fraction (0.5 g) and non-eluted fraction (7.4 g) were obtained. Syringaresinol (2.08 mg) was isolated by fractionating the methanol eluted fraction with an Amberlite XAD2 column (Organo) followed by preparative HPLC (column: Capcell Pak C18 AQ, Shiseido, detection: UV 210 nm, mobile layer: $CH_3CN/H_2O$ mixture).

The invention claimed is:

1. A method for treating a human suffering from excessive lymphatic vessel dilation comprising administering to said human an amount effective to reduce excessive lymphatic vessel dilation in the human of an extract of *Cinnamomum cassia* blume or an extract of Siberian ginseng.

2. The method according to claim 1, wherein the extract is from *Cinnamomum cassia* Blume.

3. The method according to claim 2, wherein the extract of *Cinnamomum cassia* Blume is from a twig or a bark of *Cinnamomum cassia* Blume.

4. The method according to claim 2, wherein the extract of *Cinnamomum cassia* Blume is an aqueous extract.

5. The method according to claim 1, wherein the extract is administered orally.

* * * * *